US00PP21330P2

(12) United States Plant Patent
Geerlings

(10) Patent No.: US PP21,330 P2
(45) Date of Patent: Sep. 28, 2010

(54) ***PHLOX* PLANT NAMED 'NADIA'**
(50) Latin Name: *Phlox paniculata*
Varietal Denomination: Nadia

(75) Inventor: Peter Geerlings, Hillegom (NL)

(73) Assignee: Compass Plants B.V., Hillegom (NL)

( * ) Notice: Subject to any disclaimer, the term of this patent is extended or adjusted under 35 U.S.C. 154(b) by 0 days.

(21) Appl. No.: 12/455,063

(22) Filed: May 27, 2009

(51) Int. Cl.
*A01H 5/00* (2006.01)

(52) U.S. Cl. ..... Plt./320
(58) Field of Classification Search ..... Plt./320
See application file for complete search history.

*Primary Examiner*—Susan B McCormick Ewoldt
(74) *Attorney, Agent, or Firm*—C. A. Whealy

(57) ABSTRACT

A new and distinct cultivar of *Phlox* plant named 'Nadia', characterized by its upright plant habit; dark-green colored leaves; freely flowering habit; red purple-colored flowers; and good cut flower and garden performance.

2 Drawing Sheets

Botanical designation: *Phlox paniculata.*
Cultivar denomination: 'NADIA'.

BACKGROUND OF THE INVENTION

The present invention relates to a new and distinct cultivar of *Phlox* plant, botanically known as *Phlox paniculata* and hereinafter referred to by the name 'Nadia'.

The new *Phlox* plant originated from a cross-pollination of two unnamed proprietary selections of *Phlox paniculata*, not patented, in 2002. The new *Phlox* was discovered and selected by the Inventor as a single flowering plant from within the progeny of the stated cross-pollination grown in a controlled greenhouse environment in Hillegom, The Netherlands in July, 2004.

Asexual reproduction of the new *Phlox* plant by cuttings in a controlled greenhouse environment in Hillegom, The Netherlands since 2006, has shown that the unique features of this new *Phlox* plant are stable and reproduced true to type in successive generations.

SUMMARY OF THE INVENTION

Plants of the new *Phlox* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Nadia'. These characteristics in combination distinguish 'Nadia' as a new and distinct cultivar of *Phlox:*

1. Upright plant habit.
2. Dark-green colored leaves.
3. Freely flowering habit.
4. Red purple-colored flowers.
5. Good cut flower and garden performance.

Plants of the new *Phlox* and the parent selections differ primarily in leaf and flower color.

Plants of the new *Phlox* can also be compared to plants of *Phlox paniculata* 'Starfire', not patented. In side-by-side comparisons conducted in Hillegom, The Netherlands, plants of the new *Phlox* and 'Starfire' differed primarily in leaf and flower color as plants of 'Starfire' had lighter green-colored leaves and red-colored flowers. In addition, plants of the new *Phlox* were shorter than plants of 'Starfire'.

BRIEF DESCRIPTION OF THE PHOTOGRAPHS

The accompanying colored photographs illustrate the overall appearance of the new *Phlox* plant, showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of a typical flowering plant of 'Nadia' grown in a container.

The photograph at the top of the second sheet is a close-up view of typical flowers of 'Nadia'.

The photograph at the bottom of the second sheet is a close-up view of a typical leaf of 'Nadia'.

DETAILED BOTANICAL DESCRIPTION

The aforementioned photographs and following observations, measurements and values describe plants grown in Hillegom, The Netherlands, under commercial practice during September in an outdoor nursery with day temperatures ranging from 12° C. to 32° C. and night temperatures ranging from 4° C. to 16° C. Plants were one year old when the photographs and description were taken. In the following description, color references are made to The Royal Horticultural Society Colour Chart, 2001 Edition, except where general terms of ordinary dictionary significance are used.

Botanical classification: *Phlox paniculata* 'Nadia'.

Parentage:

*Female, or seed, parent.*—Unnamed proprietary selection of *Phlox paniculata*, not patented.

*Male, or pollen, parent.*—Unnamed proprietary selection of *Phlox paniculata*, not patented.

Propagation

*Type.*—By cuttings.

*Time to initiate roots.*—About three weeks at 20° C.

*Root description.*—Fine, fibrous; white in color.

Plant description:

*Plant form/habit.*—Upright plant habit; narrow inverted triangle; moderately vigorous growth habit; basally branching habit, about five basal branches per plant.

*Plant height.*—About 47.3 cm.

*Plant width* (*spread*).—About 30.9 cm.

*Lateral branches.*—Length: About 29.1 cm. Diameter: About 4 mm. Internode length: About 3 cm. Strength: Strong. Texture: Smooth, glabrous. Color: Close to N186B to N186C; below the nodes, flushed with close to 145B.

Foliage description:

*Arrangement.*—Opposite, simple.

*Length.*—About 8.6 cm.

*Width.*—About 3.5 cm.

*Shape.*—Elliptic to ovate.

*Apex.*—Acute.

*Base.*—Attenuate.

*Margin.*—Slightly revolute and finely serrate.

*Texture, upper and lower surfaces.*—Smooth, glabrous.

*Venation pattern.*—Pinnate.

*Color.*—Developing leaves, upper surface: Close to N186A. Developing leaves, lower surface: Close to N186A to N186B. Fully expanded leaves, upper surface: Close to 137A; venation, close to 144A. Fully expanded leaves, lower surface: Close to 147B flushed with close to 200B; venation, close to 146B to 146C.

*Petiole.*—Length: About 3 mm. Diameter: About 3 mm by 2 mm. Texture, upper and lower surfaces: Smooth, glabrous. Color, upper surface: Close to N186C. Color, lower surface: Close to 146C.

Flower description:

*Flower type/habit.*—Single rotate and salverform flowers arranged in compound terminal panicles; flowers face upright and outward; panicles roughly conical in shape; freely flowering habit with about 100 flower buds and flowers developing per inflorescence.

*Fragrance.*—Faintly fragrant; sweet and pleasant.

*Natural flowering season.*—Continuously flowering from July through September in The Netherlands.

*Postproduction longevity.*—Flowers last about ten days on the plant and about ten days as a cut flower; flowers not persistent.

*Flower buds.*—Height: About 1.8 cm. Diameter: About 4 mm. Shape: Narrowly oblanceolate. Color: Close to 71A to 71B; towards the base, close to between 77A and N186C.

*Inflorescence height.*—About 16.8 cm.

*Inflorescence diameter.*—About 13.8 cm.

*Flower diameter.*—About 3.1 cm.

*Flower depth.*—About 3.2 cm.

*Petals.*—Quantity per flower: Typically five in a single whorl; petals fused at the base into a narrow tube. Length: About 3.9 cm. Lobe width: About 1.5 cm. Shape: Spatulate. Apex: Bluntly retuse. Margin: Entire. Texture, upper and lower surfaces: Smooth, glabrous.

*Color.*—Developing petals, upper surface: Darker and more intense than N57A; throat, close to N79C. Developing petals, lower surface: Close to N57C; tube, close to N79C. Fully expanded petals, upper surface: Darker and more intense than N57A; throat, close to N79C; color does not fade with development. Fully expanded petals, lower surface: Close to N57C; tube, close to N79C.

*Sepals.*—Quantity per flower: Typically five in a single whorl, fused towards the base; campanulate calyx. Length: About 9 mm. Width: About 1.7 mm. Shape: Lanceolate. Apex: Narrowly apiculate. Margin: Entire. Texture, upper and lower surfaces: Smooth, glabrous. Color, developing and fully expanded sepals, upper surface: Close to 147B; towards the margins, close to N77B. Color, developing and fully expanded sepals, lower surface: Close to between N77A and N186C.

*Peduncles.*—Length: About 14.7 cm. Diameter: About 3 mm. Angle: Erect. Strength: Strong. Texture: Smooth, glabrous. Color: Close to N186C.

*Pedicels.*—Length: About 5 mm. Diameter: About 1 mm. Angle: About 30° from vertical. Strength: Strong. Texture: Smooth, glabrous. Color: Close to 146B.

*Reproductive organs.*—Stamens: Quantity per flower: Typically five; fused with petals in throat. Filament length: About 2 mm. Anther shape: Oblong. Anther length: About 1.5 mm. Anther color: Close to 8D. Pollen amount: Scarce to moderate. Pollen color: Close to 11D. Pistils: Quantity per flower: One. Pistil length: About 2.1 cm. Stigma shape: Three-parted. Stigma color: Close to 150D. Style length: About 1.9 cm. Style color: Close to N186C. Ovary color: Close to 143A.

*Seed/fruit.*—Seed and fruit development have not been observed.

Disease/pest resistance: Plants of the *Phlox* have not been observed to be resistant to pathogens and pests common to *Phlox*.

Garden performance: Plants of the new *Phlox* have been observed to have good garden performance and tolerate rain, wind and temperatures ranging from about −30° C. to about 35° C.

It is claimed:

1. A new and distinct *Phlox* plant named 'Nadia' as illustrated and described.

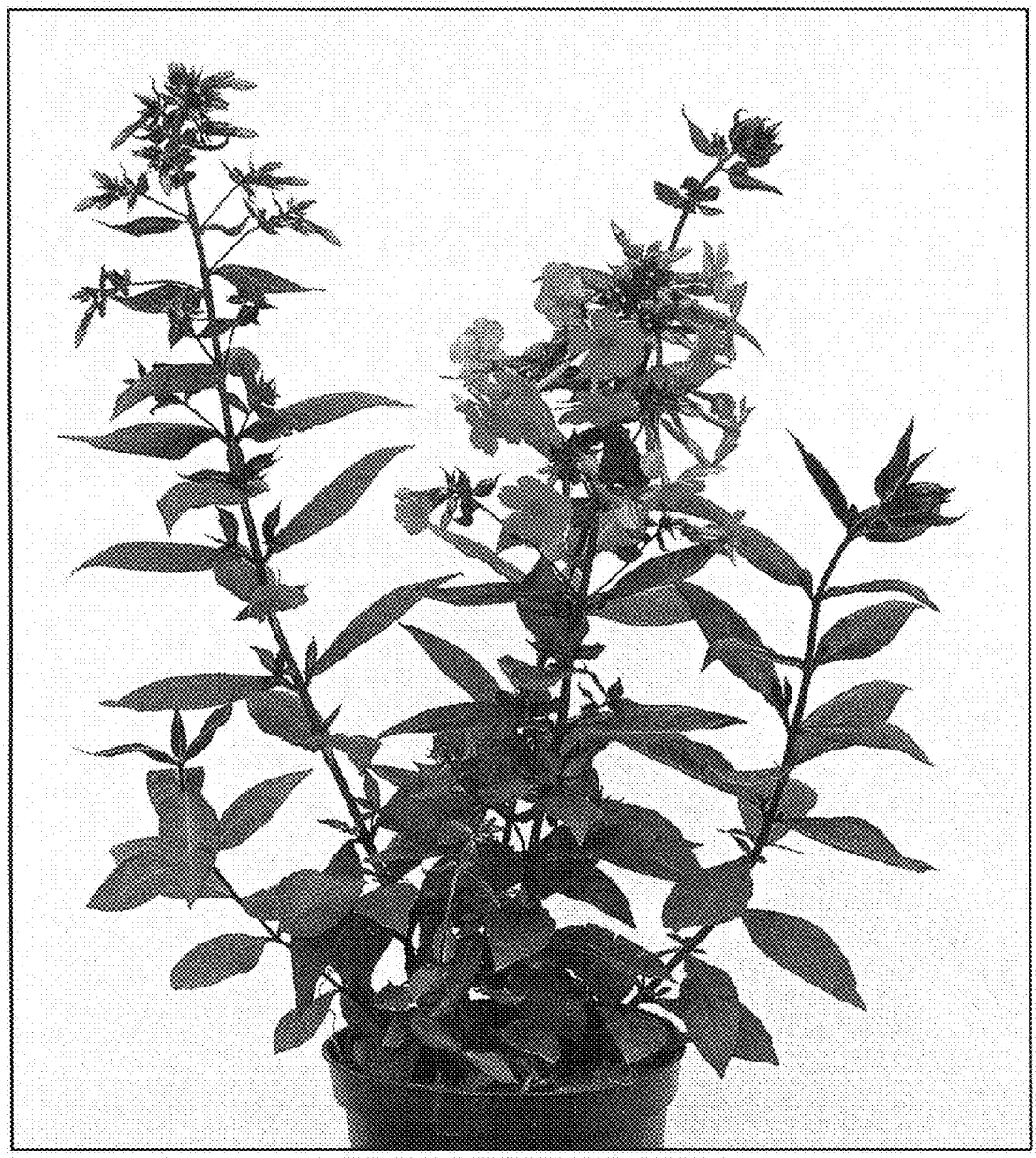

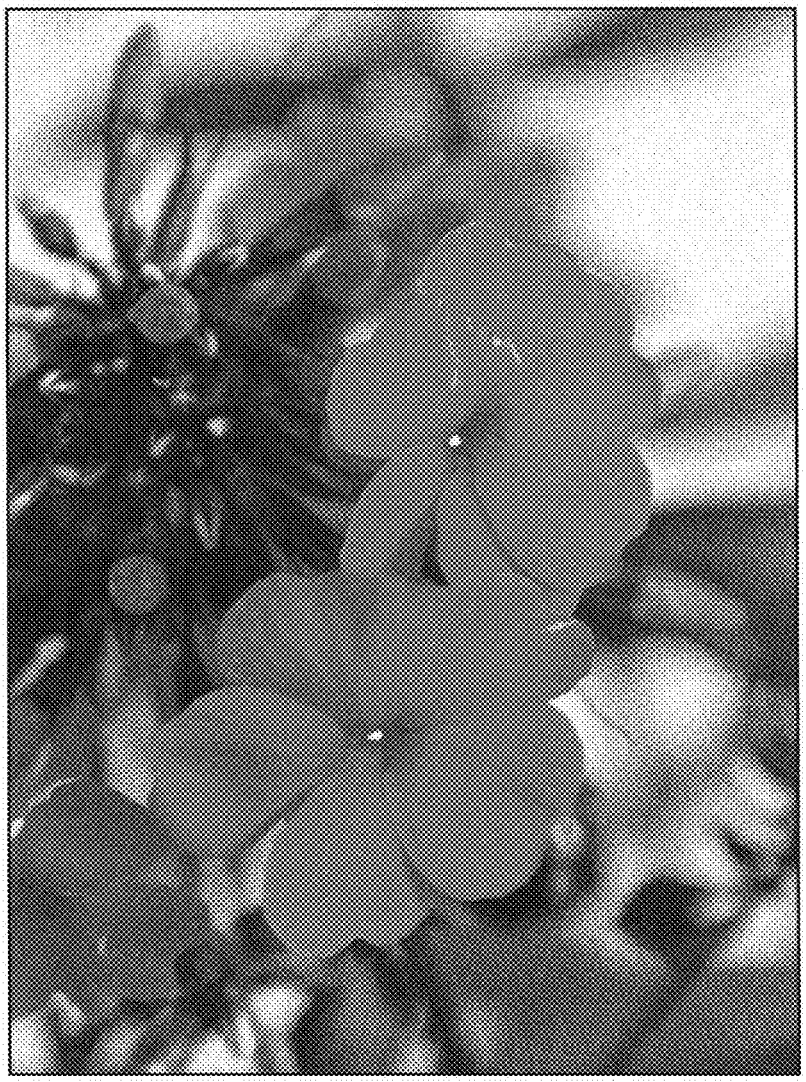
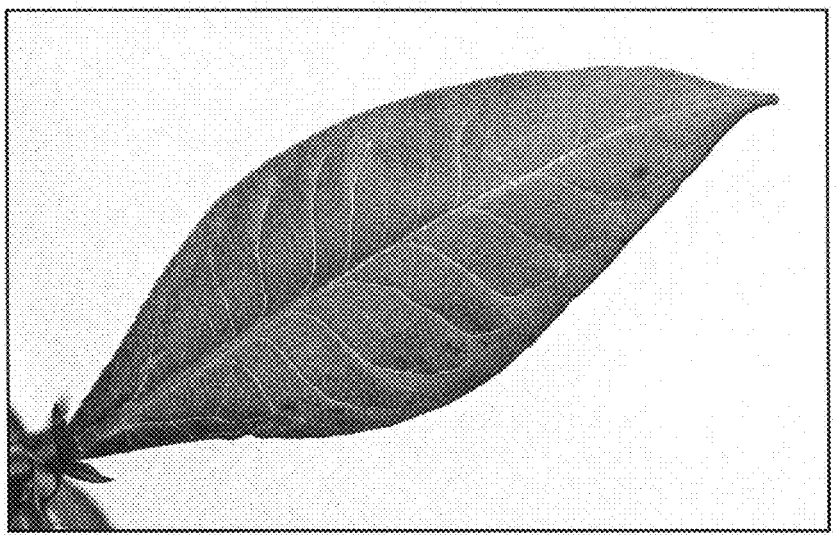

* * * * *